United States Patent [19]

Crane

[11] 4,443,075
[45] Apr. 17, 1984

[54] STABILIZED VISUAL SYSTEM

[75] Inventor: Hewitt D. Crane, Portola Valley, Calif.

[73] Assignee: SRI International, Menlo Park, Calif.

[21] Appl. No.: 277,626

[22] Filed: Jun. 26, 1981

[51] Int. Cl.³ .............................................. A61B 3/14
[52] U.S. Cl. .................................... 351/209; 351/221; 351/207
[58] Field of Search ............... 351/206, 207, 208, 209, 351/210, 221; 128/303.17

[56] References Cited

U.S. PATENT DOCUMENTS 3,591,250 7/1971 Feinstein ............................. 350/500
3,804,496 4/1974 Crane et al. .......................... 351/210
4,264,152 4/1981 Crane .................................... 351/210

Primary Examiner—John K. Corbin
Assistant Examiner—Paul M. Dzierzynski
Attorney, Agent, or Firm—Urban H. Faubion

[57] ABSTRACT

A stabilized visual system for directing a beam of energy, such as a laser beam, to a specific selected location in an eye and maintaining the beam in the selected location regardless of eye movements. The system employs a fundus illumination and monitoring device which illuminates the fundus of an eye and allows an observer simultaneously to observe the illuminated fundus, an eye tracker which continuously measures the position and changes in position of the illuminated eye and produces electrical signals in response to the changes in position of the eye, and an input beam stabilizer which directs a beam of electromagnetic energy to a selected location in the eye. Servomotor driven optical elements (e.g., a pair of mirrors) are positioned in the path of the beam of electromagnetic energy and are connected to receive and be driven by the electrical signals produced by the eye tracker so that the electromagnetic beam is maintained at the specific selected location in the eye even though the eye moves.

2 Claims, 5 Drawing Figures

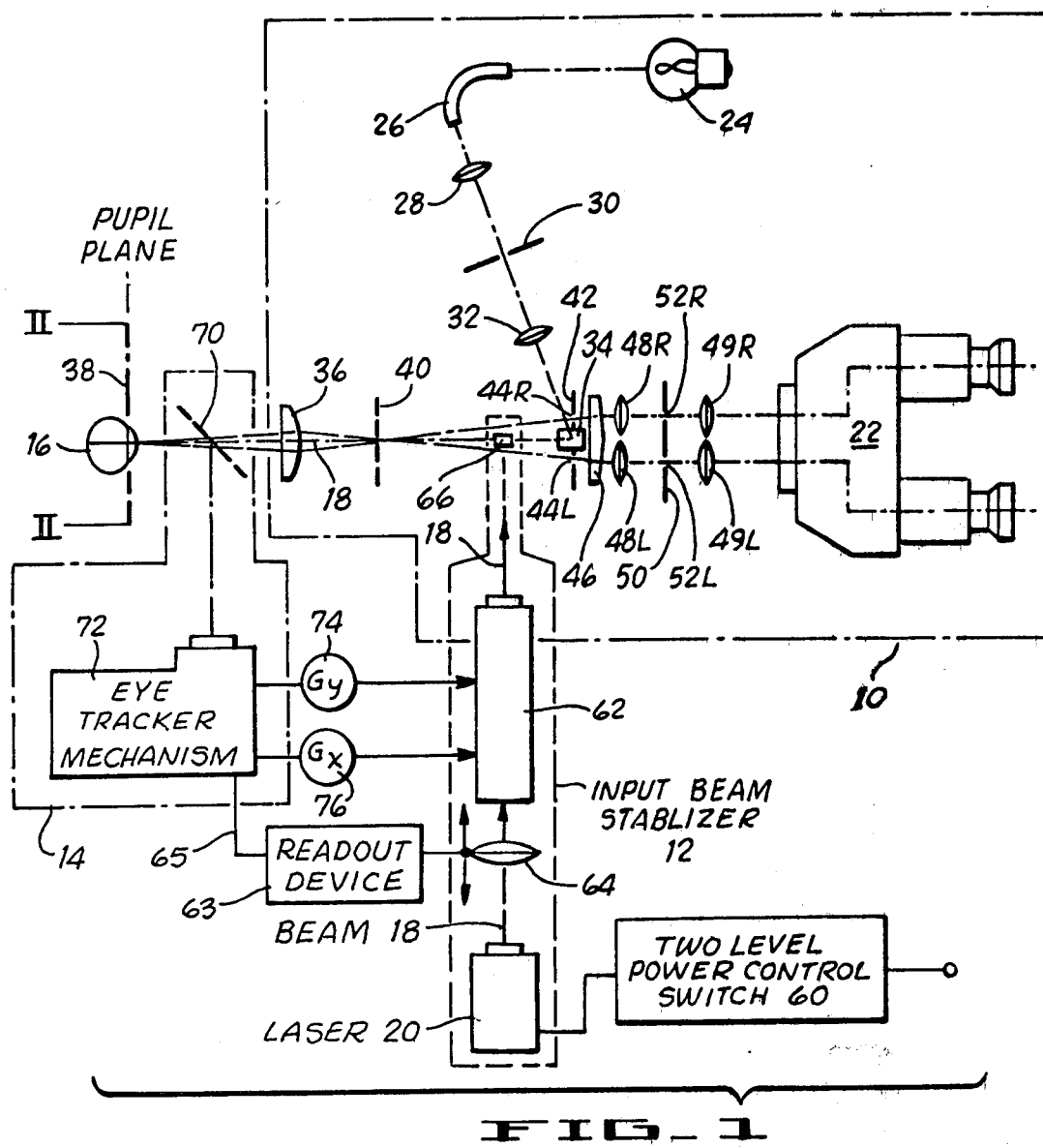
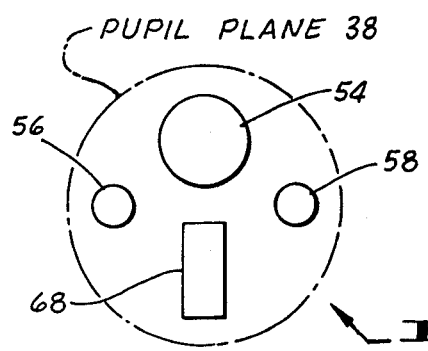

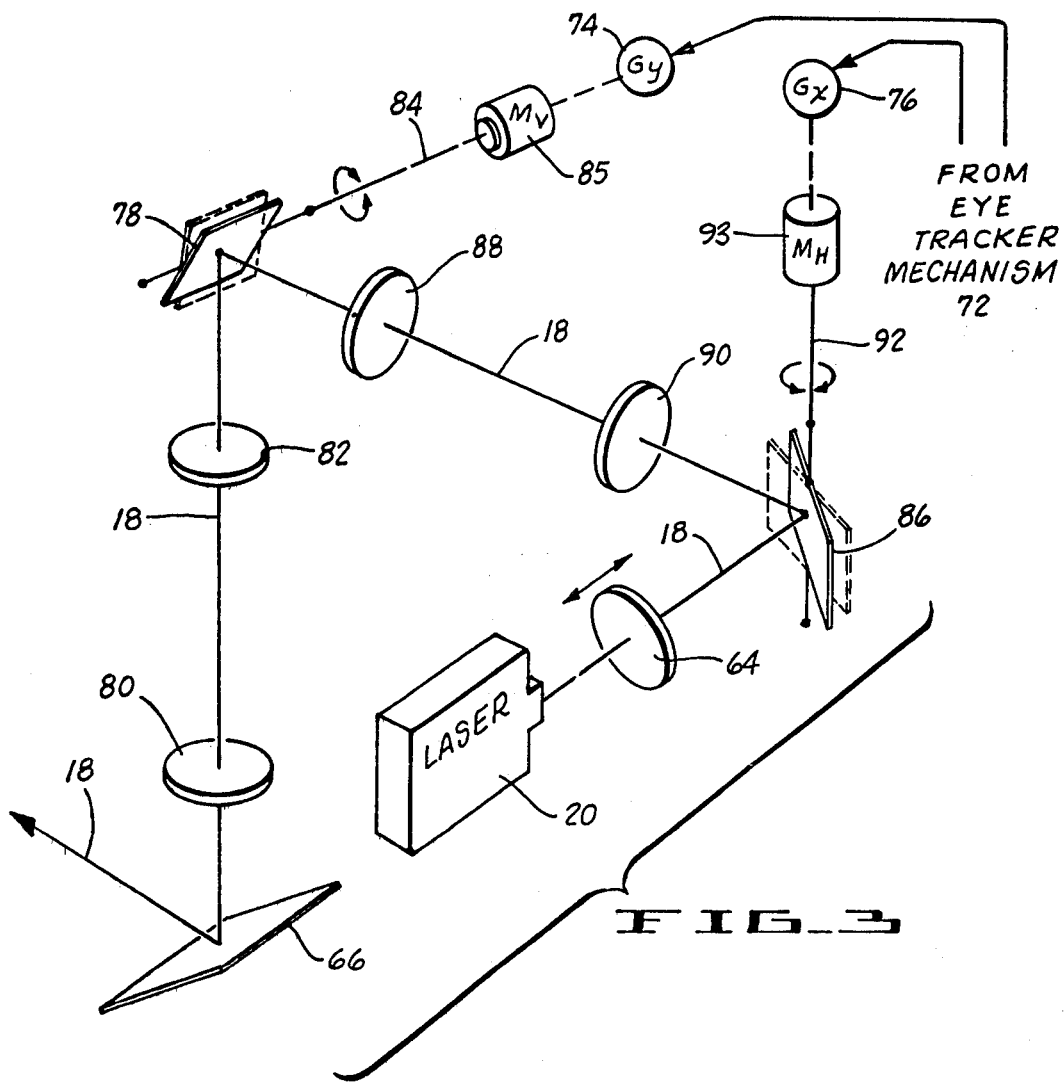
FIG_3
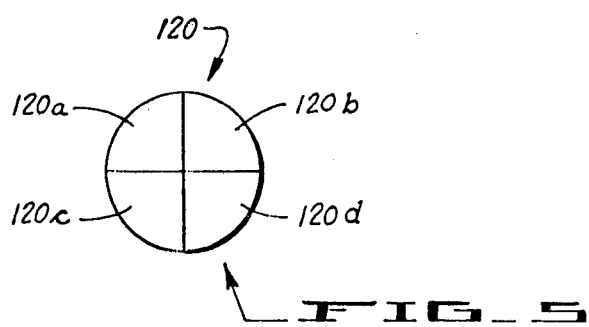
FIG_5

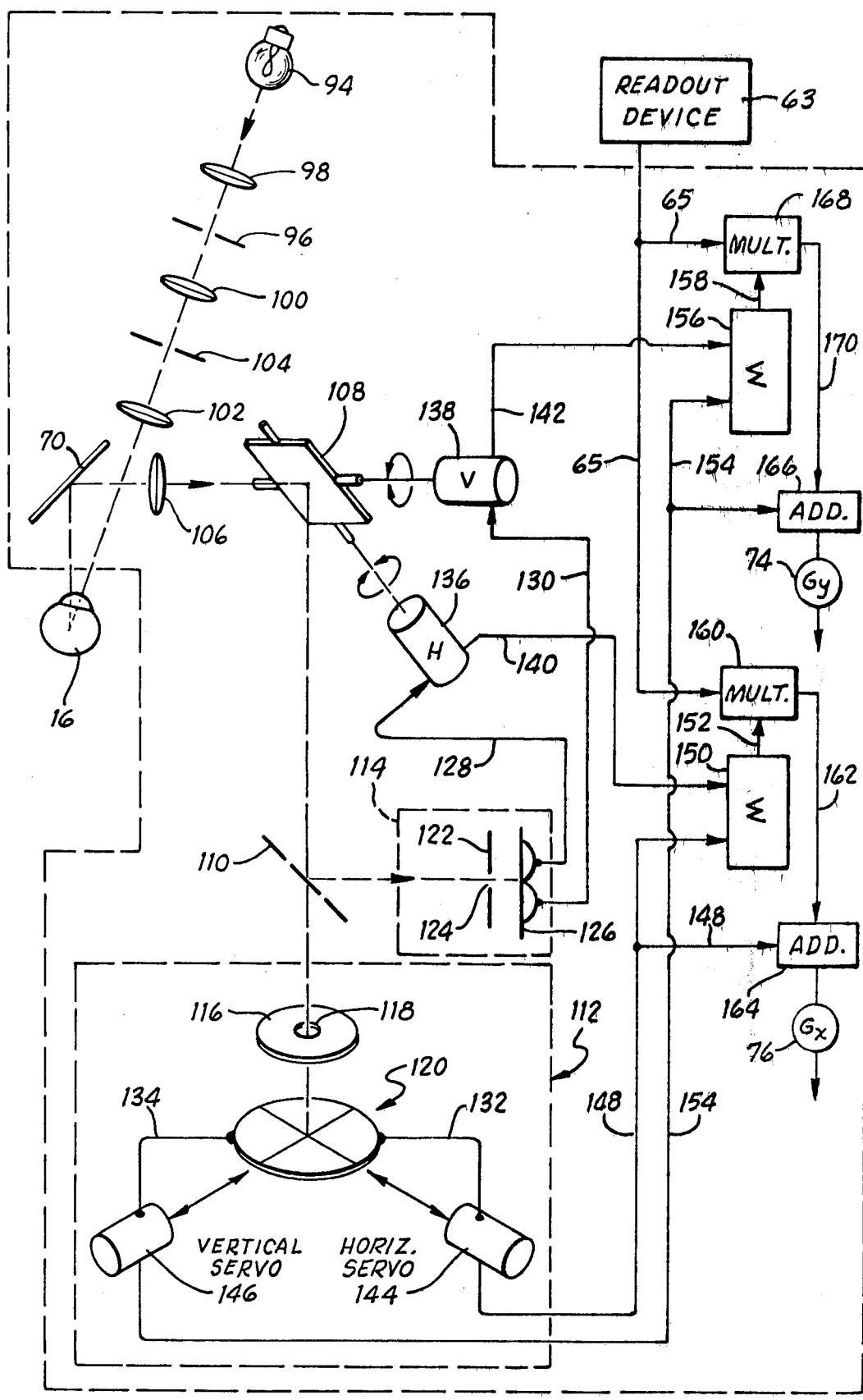
FIG_4

STABILIZED VISUAL SYSTEM

BACKGROUND OF THE INVENTION

There are many applications in ophthalmological research and treatment which require directing a beam of energy—such as a laser beam or an image projecting liquid beam—to a selected location on or in the eye of a subject or patient. In such applications the need often is to maintain the directed beam in the specific selected location regardless of eye movements (voluntary or involuntary) on the part of the subject. Prior to this invention, no practical means of providing such fixation was known.

The need for such a stabilized visual system is particularly acute in the eye treatment known as photocoagulation (both with coherent—laser—and incoherent light). There are a number of coagulator procedures for which the clinician would like to eliminate the effects of a patient's eye movements during treatment. This important application of the invention is one having most stringent requirements; therefore, the invention is described in connection with photocoagulation (specifically laser photocoagulation). It is to be understood, however, that the invention is broadly applicable to any situation requiring that a beam be fixed (stay) at a specific location in the eye regardless of eye movements.

Laser photocoagulation is a recognized technique of modern ophthalmological practice. With this treatment, "burn" lesions are created at the fundus by means of the focused energy of a laser beam. Currently available coagulators are generally built in the style of a binocular, slit lamp apparatus with facility added for a steerable laser input. In order to direct the laser beam to the desired fundus location, means are provided for illuminating the fundus and for energizing the laser beam at low power. When the operator is satisfied with the alignment, he energizes the full power of the beam, for example, by means of a foot switch. Separate controls are available to preset the intensity and duration of each flash. An example of such a system is described and claimed in U.S. Pat. No. 3,703,176, issued Nov. 21, 1972 in the names of Arthur Vassiliadis, Harold C. Zweng, Norman A. Peppers and Lloyd E. Alterton and assigned to Stanford Research Institute, now known as SRI International, and Stanford University.

Most current photocoagulation techniques depend on the use of a large contact lens placed on the eye of the patient. Although it may be possible to operate the eye tracker satisfactorily in the presence of such a contact lens, a preferred method would not require a contact lens to be used.

The fundus illumination and monitoring system shown here, which includes means for entering a steerable laser beam, was developed by the Eye Research Institute of Boston. The main feature of this photocoagulation method is that it does not require the use of a contact lens on the eye of the patient. A primary motivation in developing this technique was to improve the optical quality of the photocoagulation system, inasmuch as the contact lens causes large variations in the shape of the laser beam reaching different locations of the fundus. The fact that this method of photocoagulation does not require a contact lens makes it preferable in a stabilized system of the type described here, although many variations are also possible.

Ophthalmologists disagree on whether a laser should be used on the eye. There is no question that the laser provides useful treatment. Some ophthalmologists, however, are of the opinion that the chance of damage to the eye is too great, particularly since the operator cannot follow sudden patient eye movements fast enough to be sure the beam will hit the desired area. Even the ophthalmologists who regularly use laser photocoagulation do not use the treatment under certain circumstances where it might otherwise be beneficial. For example, unless the situation is very serious, an operator will generally avoid using the laser coagulator too close to the patient's fovea, because a sudden eye movement could bring the beam onto the fovea and cause serious damage to the patient's vision. Sudden eye movements at times occur reflexively in response to the impinging high power laser beam. Therefore, in many procedures using the laser photocoagulator, fear of eye movement dictates using very short, high energy bursts of the laser beam when longer applications at a lower energy level might be more beneficial. A system which allows the laser beam pattern to be directed to a specific location within a patient's eye and maintained at that location even though the eye moves will eliminate such concerns. In some cases where the retina lifts from the choroid and fills with fluid, the treatment consists of 100% beam coverage of the affected area. If the effects of the patient's eye movements are eliminated, the instrument can be programmed, like an automatic sewing machine, to cover the area in any prescribed pattern. Or, in cases of widespread retinal detachment, where thousands of beam applications, or "stitches", are required, the procedure can be lengthy. With the patient's eye movements under control, it is possible to automate the procedure, again like an automatic sewing machine.

Getting patient's eye movements "under control" means either eliminating them by drugs, a procedure that has its own dangers and is generally avoided in clinical practice, or measuring the patient's eye movements and moving the beam so as to compensate automatically for the eye movements. The present invention takes the second approach and, as far as is known at the present time, the art does not contain other attempts to accomplish the same result using this approach.

SUMMARY OF THE INVENTION

Thus, it is an object of this invention to provide an improved instrument for diagnosing and treating disorders of the eye.

It is a more specific object of the invention to provide a means of projecting a beam to a particular selected location in the eye of a subject and automatically maintain the beam at that specific selected location regardless of eye movements.

Another object of the invention, in an especially practical application, is to provide means of projecting a laser beam into an eye for treating a specific selected location and automatically maintain the beam fixed at the selected location regardless of eye movements.

In accordance with this invention, a beam, such as a laser beam, is coupled to a fundus illuminating and monitoring device through an optical system so that the beam is delivered to a location in the eye of a subject, which locations is selected by an operator. In addition, an eye tracker is provided which continuously measures the position and changes in position of the eye of the subject and generates an output in response to those changes, which generated output is utilized to change the coupling optics so that the beam is maintained at the selected location of the subject even though the eye moves.

The novel features which are believed to be characteristic of the invention are set forth with particularity in the appended claims. The invention itself, however, both as to its organization and method of operation, together with further objects and advantages thereof, may best be understood by reference to the following description taken in connection with the accompanying drawings.

BRIEF DESCRIPTION OF THE DRAWINGS

FIG. 1 is a schematic (mostly plan) view of a stabilized visual system illustrating one embodiment of the present invention and showing elements of a fundus illuminating and monitoring system, a laser beam delivery system, and an eye tracker for detecting eye movements and causing the beam to track the eye movements;

FIG. 2 illustrates a section II—II (in FIG. 1) taken along the pupil plane of the eye of the subject and showing the intersection with the pupil plane of the binocular viewing areas, fundus illuminating light and the beam used for treatment;

FIG. 3 is a perspective view, which is also a partially schematic diagram, illustrating elements of a laser beam delivery and stabilizer system in more detail than is shown in FIG. 1 and the relation of the beam delivery and stabilizer system to the eye tracker and fundus illumination and monitoring system;

FIG. 4 is another partially schematic diagram illustrating operational elements and features of an eye tracker and its cooperative connections in the stabilized visual system; and FIG. 5 is a diagrammatic view of the segmented photosensitive plate of one of the photodetectors used in the eye tracker embodiment illustrated in FIG. 4.

DESCRIPTION OF PREFERRED EMBODIMENTS

The overall stabilized visual system 1 is illustrated schematically in FIG. 1. The major system components are designated in three dashed line blocks which overlap to some extent. The stabilized visual system includes a fundus illumination and monitoring device, generally included in dashed line block 10; a beam input and stabilizer system enclosed in dashed line block 12; and an eye tracker incorporated in the dashed line block 14. The fundus illumination and monitoring device 10 illuminates the fundus of an eye 16 and allows an observer (not shown) to observe the illuminated fundus. The beam input and stabilizer system 12 allows a beam 18, such as a beam from a laser 20, to be delivered to a specific location in the eye 16 of a subject as observed through the fundus illumination and monitoring device 10, and the eye tracker 14 measures movements of the eye 16, generates signals responsive to the eye movements and delivers them to a servo system (described below) in the beam input and stabilizer system 12, which maintains the beam on the specific selected location even if the eye moves.

First consider the fundus illuminating and monitoring device 10, which is, in many ways, like a standard binocular fundus camera. Since an understanding of the invention requires an understanding of the use of the fundus illuminating and monitoring device 10, its modifications and cooperation with the other major components of the stabilized visual system 1, a description is given here. In the embodiment illustrated, a continuous binocular view of the fundus of the eye is provided through binoculars 22. The binocular view is not essential in the present application but is helpful to the observer and is generally available using the conventional fundus camera or slit lamp laser photocoagulator.

Light for viewing the fundus of the eye 16 is provided by a lamp 24 brought in from above by a fiber bundle 26 (top of the figure), focused by a lens 28 onto an input light diaphragm 30, which is, in turn, imaged by a diaphragm imaging lens 32 onto a 45° sloping fundus illuminating mirror 34. Fundus illuminating mirror 34 reflects the downward directed input light into the eye 16 through an imaging and focusing lens 36 which forms an image of fundus illuminating mirror 34 in the pupil plane 38 of the eye 16. For the application illustrated, the image of the illuminating source on fundus illuminating mirror 34 is adjusted to have a diameter of approximately 8 mm. Imaging and focusing lens 36 is an aspheric, plano-convex lens, specially designed for high quality imaging and focusing. The reason for this requirement will become clear from the discussion of its functions given below.

Light reflected from the fundus passes back out through the pupil of the eye 16 and is focused by plano-convex imaging and focusing lens 36 in plane 40, which is both conjugate with the retina and coincident with the plane of convergence of the binocular viewing paths. Traveling back beyond this plane (40) toward the viewing binoculars 22, each path of the binocular viewing system passes first through a stop plate 42 having a pair of apertures 44R (upper path in FIG. 1) and 44L (lower path), which constitute stops in the viewing paths. Note here that both binocular viewing paths contain the same optical elements and FIG. 1 is a plan view of the binoculars. Therefore, the upper and lower paths are right-eye view and left-eye view, respectively, and the matched elements in the two paths are given identical reference numerals followed by the letter R or L to indicate the view (or path) of the right and left eye, respectively.

Just beyond the viewing stop plate 42 is a converging prism 46 that converges the two viewing paths at the plane 40, which is conjugate with the retina of the eye 16. The stops 44R and 44L (just in front of the converging prism 46) are located in the same plane as fundus illumination mirror 34 and, therefore, are also focused in the pupil plane 38 of the eye 16. In the embodiment illustrated, viewing stops 44R and 44L are 4 mm in diameter and define the limiting aperture for each binocular viewing path; the image of each of these stops in the pupil plane 38 is approximately 1 mm in diameter. That is to say, looking back the other way, only light passing back out of the eye through these 1 mm portions of the pupil is available in the retinal images thus formed (viewed). Any input light reflected from the corneal surface cannot enter the output viewing path so long as the image of input or illuminating light diaphragm 30 does not intersect the viewing apertures in the plane 38 of the eye pupil. The reason for the special design of plano-convex imaging and focusing lens 36—a point referred to previously—is to maximize the isolation between the input and output light paths and thereby minimize the very bright reflected corneal light from the output paths. The only element common to the input and output paths is the imaging and focusing lens 36, which is specially coated to reduce reflections and hence reduce optical interference, or "noise", between illuminating and viewing systems.

Again, following the binocular viewing paths, the fundus images emanating from the prism 46 in the two viewing paths are focused by lens 48R and 48L, respectively, in the plane occupied by a stop plate 50 with a pair of apertures 52R and 52L. Apertures 52R and 52L are, in practice, adjustable irises which define the field of view of the operator. The fundus images at the field of view defining apertures 52R and 52L are relayed to optics of the operator's binoculars 22 by lenses 49R and 49L. The binoculars 22 are not illustrated in detail since they are conventional, adjustable ocular viewing binoculars.

Consider at this point the effect of the system thus far at the pupil plane 38 of eye 16. As seen in the front view of the pupil plane 38 (FIG. 2), the input illumination flooding the fundus of the eye 16 is delivered from the fiber bundle 26 and passes through a circular area 54 about 3 mm in diameter centered along the central vertical axis in the upper region of the pupil plane 38. The binocular viewing system works through two lateral, circular areas 56 and 58 approximately 1 mm in diameter at opposite sides of the pupil plane 38. Isolation of light input and viewing areas at the pupil plane 38 results in virtually eliminating interference between illuminating and viewing systems.

Requirements of the system (as shown) are that the beam from a laser 20 which is to be used in treatment of the eye 16 be focused on the retina, be adjustable in position by the system operator so that it can be directed to a selected location within the eye 16, and that its position be controllable in response to eye movements so that it can be maintained at the selected location in the eye 16. A broad understanding of these functions and the synergistic cooperation of system elements is had by reference to the beam input and stabilizer portion (broken line box labeled "12") of FIG. 1.

The laser 20 generates beam 18 when power is applied by closing a two level power control switch 60 to apply the required energizing voltage (source not shown). The switch 60 is provided with two levels since the laser 20 is first energized at low level for viewing and beam adjustment and then energized to deliver a high energy beam for treatment. The beam 18 is first passed through a manually adjustable beam focusing lens 64 and into an input beam stabilizer mechanism, indicated diagrammatically in FIG. 1 by a box labeled 62. The function of the input beam stabilizer 62 is to control the beam 18 in response to eye movements. The arrangement for accomplishing this function is described in detail below in connection with FIG. 2, but for simplification of the description details are omitted here.

Leaving the input beam stabilizer 62, the beam 18 is brought into fundus illuminating and monitoring device 10 and deflected into the eye 16 via deflecting mirror 66 which is located, from a plan view, on the center line of the binocular viewing system 10 between the fundus illuminating mirror 34 and the retina conjugate plane 40. The beam deflecting mirror 66 is between the converging lines of binocular view and also below the illuminating beam reflected to the eye 16 by fundus illuminating mirror 34 and, therefore, does not interfere either with fundus illumination or viewing. The beam deflecting mirror 66 is also axially positioned to be in focus nominally at the nodal point of the eye 16 (almost coincident with the center of curvature of the cornea); this leads to minimum variation in the shape of the beam 18 on the retina as it (beam 18) is swept to different locations. The laser beam 18 is focused at the retina conjugate plane 40 by the laser beam focusing lens 64. That is, compensation for the axial variation in the position of the retina conjugate plane 40 with the refractive condition of the subject is adjusted by changing the axial position of lens 64.

Both the focusing of the beam 18 on the eye and adjustment of beam deflecting mirror 66 (or alternatively, the mirrors within input beam stabilizer 12) to select the location it strikes the eye 16 are made at low laser power and while viewing the beam 18 through the binocular viewing system 10. Neither the means for adjusting the gimbaled beam deflecting mirror 66 nor the means for moving beam focusing lens 64 are illustrated in detail since they are entirely conventional and form no part of the present invention. For example, a joy stick lens moving arrangement, as is conventional on many commercial laser photocoagulators, is used to move beam focusing lens 64 in one practical embodiment of the invention. However, in order properly to correct beam position in response to the patient's eye movements, a signal indicative of the axial position of the focusing lens 64, and therefore of the refractive error of the subject, is connected by lead 65 to be incorporated with beam corrective output signals from the eye tracker mechanism 72, as will subsequently be explained in more detail in connection with FIG. 4.

Entry of the laser beam 18 to the eye 16 is confined to a small region of the lower pupil, as indicated by the rectangular area 68 (FIG. 2) on the central vertical diameter and below the horizontal diameter of the circular pupil plane 38. The projections on the pupil plane 38 of the illumination source image 54, viewing apertures or areas 56 and 58, and the laser beam area occupy an area of the pupil on the order of 4 to 5 mm in diameter, and the patient's pupil must ordinarily be dilated for all procedures involving this instrument. Note again that these projections on the pupil plane 38 do not overlap, and thus interference problems are avoided.

Next consider the functional operation of eye tracker 14 which measures movements of the eye 16 and generates corrective signals to cause the applied beam 18 to maintain the position in the eye 16 as selected by the operator even though the eye 16 moves. FIG. 1 shows the eye tracker 14 diagrammatically and its connections, physical and electrical, in the stabilized visual system.

Although the specific type of eye tracker used here is not a limitation on the inventive concept, the double Purkinje image method is preferred for its accuracy and a two dimensional (as opposed to a three dimensional—see reference below to "Accurate Three-Dimensional Eyetracker") eye tracker is selected for both adequacy and simplicity. At least a two dimensional eye tracker is a necessity. Corneal and lumbus eye trackers can record very small eye movements, but their accuracy is poor. This inaccuracy arises from eye translation movements, which are indistinguishable from eye rotation movements. For example, 0.1 mm of eye translation causes approximately a 1° artificial signal in the eye rotation record from a corneal reflection or limbus eye tracker. Furthermore, the limbus eye tracker cannot be used since it records eye movements effectively only in the horizontal direction. The double Purkinje method of eye tracking eliminates the translation artifact from the eye rotation measurement.

The double Purkinje image eye tracker operates on reflections formed by the anterior surface of the cornea and the posterior surface of the eye lens, which images as known as the first and fourth Purkinje reflections, respectively. The first image, which is virtual, and the fourth, which is real, are both formed approximately in the pupil plane 38 of the eye 16 and move by the same amount with eye translation but differentially with eye rotation. By monitoring the spatial separation of these two images, eye rotation can be measured accurately without being confused by translation. Similarly, eye translation can be measured accurately without being confused by eye rotation.

Discussion of these factors, including formation and location of the Purkinje images, is found in the paper "Accurate Two-Dimensional Eye Tracker Using First and Fourth Purkinje Images", JOSA, v. 63, n. 8 (Aug. 1973), pp. 921-928, by T. N. Cornsweet and H. D. Crane, the paper "Accurate Three-Dimensional Eyetracker", App. Optics, v. 17, n. 5 (Mar. 1, 1978), pp. 691-705, by H. D. Crane and C. M. Steele, and in U.S. Pat. Nos. 3,712,716 and 3,724,932, issued Jan. 23, 1973 and Apr. 3, 1973, respectively, both in the names of Tom N. Cornsweet and Hewitt D. Crane and assigned to Stanford Research Institute, now SRI International. The eye trackers discussed in the referenced papers and disclosed and claimed in those two patents will perform very well in the present stabilized visual system, and the subject matter of these citations is specifically included herein by reference.

The instrument uses invisible infrared light and operates through a dichroic beam splitter, or mirror, 70 which is located directly in front of the eye 16 at an angle appropriate to reflect the infrared Purkinje images found in the eye 16 directly back into the eye tracker mechanism 72. A dichroic mirror 70 is chosen which transmits the visible light of the laser beam 18 and illumination source 24 and reflects the invisible infrared light from the eye tracker.

The basic optical system of the eye tracker 14 is described in detail in connection with FIG. 4 below. It will suffice for this functional description to point out that a fundamental feature of the eye tracker 14 is its ability to measure eye rotation and eye translation separately and accurately and produce vertical and horizontal output signals at independent vertical and horizontal gain controls 74 and 76, respectively, which are applied to servo systems on the input beam stabilizer 62 and cause the spot on the eye 16 produced by the laser beam 18 to move in precise synchronism with the retina, thus having the appearance—and practical effect—of being attached to a specific preselected spot on the retina. The horizontal and vertical gain controls 74 and 76 provide an adjustment to compensate for any variation in eyeball dimensions from subject to subject, which causes corresponding variation in the magnitude of output signal for a given magnitude of eye movement.

The above description covers the overall functional operation of the stabilized visual system and details of the fundus illuminating and viewing system. Next refer to FIG. 3 for details of the input stabilizer 62 which receives the output signals from the eye tracker 14 and maintains the laser beam pattern (spot) at the selected location on the eye 16 in response thereto. A practical input stabilizer for this application is the one disclosed and claimed in a copending patent application, Ser. No. 014,989, entitled VISUAL STIMULATOR, filed Feb. 26, 1979 in the name of the present inventor and assigned to the assignee of the present application. This application issued Apr. 21, 1981 as U.S. Pat. No. 4,264,152. The same deflector is shown and described in detail in "Three Dimensional Visual Stimulus Deflector" by H. D. Crane and Michael R. Clark, App. Optics, v. 17, n. 5 (Mar. 1, 1978), pp. 706-714. The contents of both the article and U.S. Pat. No. 4,264,152 are specifically incorporated herein by reference.

Common elements of FIGS. 1 and 3 are given the same reference numerals; therefore, orientation of the stabilizer elements relative to the components of the overall stabilized visual system 1 of FIG. 1 may be had by noting the relative location of these elements. Specifically, the laser source 20 and the beam focusing lens 64 (at the right side of FIG. 3 and bottom of FIG. 1, as shown) and the beam deflecting mirror 66 (at the left side of FIG. 3 and on the central axis of the binocular system as shown in FIG. 1) are common to both figures.

Recall that the beam deflecting mirror 66 is positioned to be in focus nominally at the nodal point of the eye 16. Mirror 66 is reimaged on the horizontal axis of rotation of rotatably mounted vertical position correction mirror 78. The image at vertical position correction mirror 78 is formed by a pair of identical lenses 80 and 82, separated by the sum of their focal lengths and preferably located a focal length from the axis of the closest adjacent mirror. A pair of identical lenses, separated by the sum of their focal lengths and so positioned, leads to a nominally undistorted unity magnification image (unity and undistorted relative to the input image).

Vertical position correction mirror 78 is rotated by its shaft 84 in response to the output of the eye tracker vertical gain control 74, which, in turn, receives the vertical correction signal generated by the eye tracker 14. This shaft rotation is accomplished by connecting the output of the vertical gain control 74 to a servo motor 85.

Movement of the mirror 78 deflects the incident laser beam 18 so that the beam spot is positioned, by way of the beam deflecting mirror 66, to the proper vertical position on the eye 16 itself. The servo motor 85 which rotates the vertical position correction shaft 84 may be any one of a number of conventional servo motors. In the instrument actually used, a conventional galvanometer movement is employed.

In front of the vertical position correction mirror 78 (toward laser 20) another nominally undistorted unity magnification image of mirror 66 is provided at a horizontal position correction mirror 86 which is mounted for rotation about its central vertical axis. Again, the image is provided by including a pair of identical magnifying lenses 88 and 90, separated by the sum of their focal lengths and each preferably located a focal length from the vertical position correction mirror 78 and horizontal position correction mirror 86. Thus, the eye's nodal point nominally falls on the axis of rotation of horizontal position correction mirror 86. Horizontal position correction mirror 86 is rotated about its vertical shaft 92 by a second servo motor 93 to produce horizontal deflection of the laser beam 18. The proper horizontal correction of laser beam 18 is assured since the vertical position correction mirror shaft 92 is rotated in response to the output of the horizontal gain control 76, which, in turn, receives the horizontal correction signal generated by the eye tracker 14. That is, output of horizontal gain control 76 is connected to the servo motor 93 which controls rotary motion of the horizontal position correction mirror drive shaft 92 and, consequently, the rotary position of mirror 86. Movement of the mirror 86 deflects the laser beam 18 so that the beam spot is positioned, by way of the vertical position correction mirror 78 and beam deflecting mirror 66, to the proper horizontal position on the eye 16. Like the vertical position correction servo motor 85, servo motor 93, which rotates horizontal position correction shaft 84, is conventional.

With the axes of rotation of horizontal and vertical position correction mirrors 86 and 78, respectively, nominally conjugate to mirror 66, it is seen that a beam directed through the beam stabilizer system 12 can be directed to a given selected position on (or in) the eye 16, just as though mirror 66 itself were so rotated. In addition, the beam can be moved in response to vertical and horizontal correction signals delivered to the eye tracker 14.

The beam focusing lens 64 (see FIG. 1) is moved axially to assure that the beam 18 is focused in retinal image conjugate plane 40 and, thus, also at the retina of eye 16. As previously pointed out, under certain circumstances it is necessary to compensate or correct for effects of refractive error of patients. In order to provide these corrections a readout device 63 is connected to follow focusing lens 64 and produces a signal on its output circuit 65 which is a function of the deviation of the axial position of the lens 64 from its initial position of focus for the particular patient. The output of the circuit 65 is supplied to the eye tracker mechanism 72 and incorporated in its output as described in connection with the detailed description of FIG. 4. As a generality it can be said that this correction is required for "near-sighted" and "farsighted" patients who have "normal" vision.

For an understanding of the need for this refractive corrective measure, consider what happens when the eye 16 translates from side to side or up and down, either because of eye movement within the socket or because the head itself moves with respect to the laser beam input. Responsive to eye translation, the retinal image formed in retina conjugate plane 40 also translates from side to side or up and down, but by an amount dependent on the refractive power of the patient's eye. For an emmetrope, that is, for a subject whose accommodation relaxes precisely to infinity, the amount of movement in plane 40 is zero. This can be seen from the fact that the light between the eye 16 and lens 36 is collimated when the eye 16 is focused for infinity, and lateral movement of the eye 16 has no effect on image position in retina conjugate plane 40. Thus, the correction of beam position required due to eye translation is also zero and the output of readout device 63 is set to produce a zero output signal on its output circuit 65.

For patients who are myopic or hyperopic, however, that is, whose far point is closer than or beyond infinity, respectively, there is movement of the fundus image in retina conjugate plane 40 with translation of the eye 16. For this reason, perfect stabilization requires that the laser beam 18 move in response to eye translation as well as eye rotation. The direction and amount of beam movement required for a given amount of eye translation depend on the refractive error of the patient, that is, on whether the patient is myopic of hyperopic and by how much. The amount of readjustment required is directly related to the patient's refractive correction, which is reflected directly in the axial position of lens 64. Lens 64 is adjusted to focus the laser beam on retina conjugate plane 40, and therefore, on the patient's retina. That is, as noted earlier, the retina conjugate plane 40 is in different axial positions for different amounts of refractive error of the patient, and lens 64 is moved axially to compensate for this axial motion of the conjugate plane 40. Therefore, a readout of the axial position of the focusing lens 64 as generated on output circuit 65 of readout device 63 is a measure of the refractive error and is shown modifying the translation computation of eye tracker mechanism 72 in FIG. 4.

Next consider how the eye tracker 14 measures eye movements and generates output signals which are a function of those movements. Referring now to FIG. 4, there is shown a diagrammatic illustration of an embodiment of an eye tracker as incorporated in the stabilized visual system of this invention. For orientation, note that the eye 16 and dichroic mirror 70 are similarly oriented in both FIGS. 1 and 4. Recall that the dichroic mirror 70 does not interfere with the light or viewing paths from the fundus illuminating and binocular viewing system 10 or the laser source 20 since it passes substantially all light of those wavelengths and reflects only light in the infrared.

In the embodiment illustrated, the infrared light 94 used by the eye tracker 14 to make measurements is projected directly into the eye, and the Purkinje images so formed are reflected from the mirror 70 back into the eye tracker 14. The effective size of the infrared light source 94 is defined by projecting or imaging it directly onto a stop 96 by means of focusing lens 98. A light collimating lens 100 is positioned a focal length away from the source size determining stop 96 so that it collimates and relays the light to the next focusing lens 102 (toward the eye). Focusing lens 102 is positioned so that its focal plane is nominally coincident with the pupil plane 38 of the eye 16 and, therefore, forms an image of light source stop 96 in this plane. Purkinje image forming stop 104 is interposed in the light path between collimating lens 100 and focusing lens 102 at the focal plane of focusing lens 102 and, therefore, appears to the eye 16 at optical infinity. All of the light emerging from stop 104 passes through the image of source size determining stop 96.

First and fourth Purkinje images of Purkinje image forming stop 104 are formed approximately in the pupil plane 38 of the eye 16. In particular, a first Purkinje image is formed nominally in the pupil plane 38 of the eye 16 by the reflected component of light from the cornea of the eye 16 and a fourth Purkinje image is also formed nominally in the pupil plane 38 of the eye 16 by the reflected component of light from the rear surface of the lens of the eye 16. Both the first and the fourth Purkinje images are reflected by the reflecting surface of the dichroic mirror 70 and reimaged by an output lens 106 by way of a movable mirror 108. The mirror 108 reflects the images to a beam splitter 110, which both transmits the images to a fourth Purkinje image detection station 112 and reflects the images to first Purkinje image detector station 114. Because the first Purkinje image is much brighter than the fourth Purkinje image, beam splitter 110 reflects about 10% of the incident light toward the first Purkinje image detector station 114 and transmits approximately 90% to the fourth Purkinje image detector station 112.

The fourth Purkinje image detector station 112 includes a stop plate 116 having an aperture 118 therein and a multiple field photodetector 120 having four quadrants 120a through 120d, as in FIG. 5. In a similar fashion, the detection station 114 includes top plate 122 having an aperture 124 and a multiple field photodetector 126. The apertured plate 116 serves to mask the multiple field photodetector 120 from the first Purkinje image but allows the fourth Purkinje image to pass through the aperture 118 to the multiple field photodetector 120. Similarly, the apertured plate 122 serves to mask the multiple field photodetector 126 from the fourth Purkinje image, allowing the first Purkinje image to impinge on the multiple field photodetector 126 through the aperture 124.

The centers of the four quadrants of the multiple field photodetectors 120 and 126 are aligned with the apertures 118 and 124 in the fourth and first Purkinje image stop plates 116 and 122, respectively, and produce electrical output signals proportional to a shift of the incident beam from the centers of the quadrants. That is, the multiple field photodetectors 120 and 126 generate electrical outputs on their electrical output circuits indicative of the imbalance of the images falling thereon with respect to the four quadrants of the photodetectors. For example, an imbalance between the output of the sum of the upper two quadrants and output of the sum of the lower two quadrants of a photodetector is an indication that the image falling thereon is shifted with respect to the photodetector in a vertical direction. Similarly, an imbalance between the summed output of the right and left pairs of quadrants of a photodetector is an indication that the image falling on the photodetector is shifted in a horizontal direction with respect to the axis of the photodetector. Thus, the first Purkinje image photodetector 126 produces a horizontal error signal at its horizontal error output circuit 128 in response to any horizontal imbalance and a vertical error signal on circuit 130 in response to any vertical imbalance. In like manner, fourth Purkinje image photodetector 120 produces error signals on circuits 132 and 134 in response to horizontal and vertical imbalances, respectively.

Purkinje image reflecting mirror 108 is pivoted by a pivot assembly to rotate about both is vertical and horizontal axes. That is, the mirror is pivoted at its center and is rotatable in yaw around a central vertical axis and in pitch around a central horizontal axis. A horizontal servo system 136 is provided for rotating the mirror 108 in a horizontal direction (i.e., about its central vertical axis) and a vertical servo system 138 is provided for rotating the mirror 108 in a vertical direction (i.e., about its central horizontal axis). The horizontal servo system 136 receives as an input the position information on the electrical output circuit 128 of the multiple field photodetector 126 as to the imbalance between its horizontal pairs of quadrants, which information corresponds to horizontal displacements of the first Purkinje image with respect to the multiple field photodetector 126. The horizontal servo system provides an output signal on horizontal servo signal circuit 140 which depends upon the horizontal positon of the first Purkinje image and is proportional to a combination of rotation and translation of the eye. In a similar manner, the vertical servo system 138 receives input position information from the electrical output circuit 130 of the multiple field photodetector 126 relative to the vertical imbalance between the vertical pairs of quadrants of the photodetector, which information corresponds to vertical movement of the first Purkinje image. Vertical servo system 138 produces a signal on its output circuit 142 depending upon the vertical position of the first Purkinje image. By this arrangement, Purkinje image reflecting mirror 108 maintains the first Purkinje image centered on photodetector 126, which is spatially fixed, and signals are generated indicative of both vertical and horizontal displacement of the first Purkinje image.

The fourth Purkinje image photodetector 120 which, as previously pointed out, also functions simultaneously as a horizontally oriented split field cell and as a vertically oriented split field cell, is mounted to be translated horizontally and vertically by servo motors 144 and 146, respectively. Horizontal translating servo motor 144 is connected to receive the horizontal error signal (on circuit 132) generated by the photodetector 120, and vertical translating servo motor 146 is connected to receive the vertical error signal (on circuit 134). Thus, the photodetector 120 is driven so that the fourth Purkinje image is maintained in the center of the photodetector. In this manner photodetector 120 is servo controlled to track movement of the fourth Purkinje image relative to the first Purkinje image.

If the eye 16 translates, the Purkinje image reflecting mirror 108 is automatically repositioned to maintain the first Purkinje image centered on the first Purkinje image photodetector 126. Because the first and fourth Purkinje image reflections move through exactly the same distance with pure eye translation, the same movement properly repositions the fourth Purkinje image at the center of the fourth Purkinje image photodetector 120. Thus, with pure eye translation, no movement of the fourth Purkinje image photodetector 120 results. If the eye 16 rotates, however, the first and fourth Purkinje images move differentially and horizontal and vertical signals are generated on the horizontal and vertical error circuits 132 and 134, respectively, to cause the horizontal and vertical servo motors 144 and 146 automatically to reposition the fourth Purkinje image photodetector 120 so that the fourth Purkinje image remains at the center of the four quadrant photodetector 120. Thus, the position of the fourth Purkinje image photodetector 120 indicates the separation between the first and fourth Purkinje images at the pupil plane 38 of the eye 16 and is a measure of the two dimensional angular position of the eye 16. The horizontal and vertical servo motors 144 and 146, respectively, generate output signals which are the direct measure of the horizontal and vertical angular movement of the eye 16.

Although it is a digression at this point, note that the signals which drive the vertical servo motors 138 and 146 and horizontal servo motors 136 and 144 are generally referred to as error signals. The servo motors move until the error signals become zero. The error signals could, in principle, themselves provide a direct measure of image movement without the servos, but in that form of system (generally referred to as open loop) the magnitude and the linearity of the output signals are very sensitive to factors such as component drift and change in gain in the photodetectors 120 and 126 and other circuit elements, variation in light sensitivity across the face of the photodetectors 120 and 126, and the uniformity, shape and brightness of the light pattern. The servo motors 136, 138, 144 and 146, by maintaining each image fixed at an electrically null position on their photodetectors, eliminate sensitivity to these parameters and result in a much more stable and accurate system.

The output signals generated by horizontal and vertical servo motors 144 and 146, respectively, alone can be applied directly to the horizontal and vertical gain controls 76 and 74 to control the laser beam. It will be remembered (see FIGS. 1 and 3) that the outputs of the horizontal and vertical gain controls 76 and 74 are connected to the input beam stabilizer mechanism 62 to control the position of the spot from the laser beam 18 on the eye 16. Particularly in the above detailed description relative to FIG. 3, it is noted that the output of horizontal gain control 76 is connected to drive the horizontal position correction mirror 86 to take care of any horizontal angular correction needed, and the output of vertical gain control 74 is connected to drive the vertical position correction mirror 78 to take care of any vertical angular movement of the eye. Thus, if only the outputs generated by horizontal and vertical servo motors 144 and 146 are connected directly to the horizontal and vertical gain controls 76 and 74, the rotational beam correction is made for rotational eye movement alone. This is, in fact, one way to operate the system. It is, however, more desirable to correct for both rotation and translation of the eye 16. Therefore, additional inputs are required.

The signals generated at circuits 140 and 142, respectively, by the first Purkinje image horizontal and vertical servo motors 136 and 138 contain information relative to both eye translation and eye rotation (vertical and horizontal) and, when properly combined with the outputs from fourth Purkinje image vertical and horizontal servo motors 146 and 144, give a measure of the two dimensional translational position of the eye 16. As noted previously, the magnitude and polarity of eye translation signal that must be applied to correct the laser beam position additionally depends on the refractive error of the subject (being zero in the case of an emmetrope), which refractive error is provided by the signal generated by lens position readout device 63. By properly combining the refractive error signal with the translation output signals, proper amounts of translational eye movement corrections are provided. The corrected translational signals, when coupled with the eye rotation signals at horizontal and vertical gain controls 76 and 74, respectively, provide signals which correct for both rotational and translational eye movement.

Specifically, the horizontal rotational output signal generated by horizontal rotational servo motor 144 at its error output circuit 148 is connected both to horizontal gain control 76 and to a horizontal translational summing circuit 150. Circuit 150, a conventional summing circuit, produces a purely translational horizontal signal on its output circuit 152 by subtracting the signal containing purely horizontal rotational eye movement information (circuit 148) from the signal containing both translational and rotational horizontal eye movement information (circuit 140). Both the uncorrected purely translational horizontal signal generated on circuit 152 and the refractive error signal generated on circuit 65 by the readout device 63 (a function of the axial position of beam focusing lens 64) are connected to a conventional multiplier circuit 160. The product of these two horizontal translational signals produces a refraction corrected horizontal translational output signal on its output circuit 162 which is added to the horizontal rotational eye movement signal (on circuit 148) by a conventional adding circuit 164. The output of adding circuit 164 is supplied directly to the horizontal gain control 76.

Since horizontal gain control 76 receives the sum of the corrected horizontal translational eye movement error signal (on circuit 162) and the horizontal rotational eye movement signal (on circuit 148), its output signal contains all horizontal corrective information. The output signal from horizontal gain control 76 is, in turn, supplied to the input beam stabilizer mechanism 62 to control and correct the horizontal position of the spot from the laser beam 18 on the eye 16.

In a similar manner, an uncorrected vertical translation error signal is provided on the output circuit 158 of a vertical translational adding circuit 156. In order to accomplish this, the vertical rotational output signal generated by vertical rotational servo motor 146 at its output circuit 154 is supplied to the vertical error adding circuit 16, both of which are also conventional summing circuits. Summing circuit 156 combines the signal containing both translational (uncorrected) and rotational vertical eye movement information (circuit 142) with the signal containing purely vertical rotational information (circuit 154) to produce a purely vertical translational signal which is uncorrected for patient refractive condition. This uncorrected vertical translational signal on the output circuit 158 and the refractive error signal (on circuit 65) are connected to vertical translational multiplier circuit 168 (a conventional multiplier circuit). In this manner, a refraction corrected vertical translational signal is produced on multiplier output circuit 170.

In order to produce an output signal from vertical gain control 74 which contains all vertical corrective information, a conventional adder circuit 166 is connected to receive and combine the combination vertical translational eye movement signal, the refraction corrected signal from the vertical translation multiplier circuit 168 (on circuit 170) and the vertical rotational eye movement signal (on circuit 154). Vertical gain control 74 applies its output to the input beam stabilizer mechanism 62 to control and correct the vertical position of the spot from laser beam 18 on the eye 16.

Thus, it is seen that the objects of the invention are carried out by providing a stabilized visual system wherein a beam is directed to a specific preselected location in or on a patient's eye 16 and is maintained in the selected location even if the eye 16 moves both in rotation and translation, just as if the pattern of the beam were fixed to the eye 16.

While particular embodiments of the invention have been shown and described here, it will, of course, be understood that the invention is not limited to these particular arrangements, since many modifications, both in the circuit arrangements and in the instrumentalities employed, may be made. For example, the invention has been illustrated and described using the laser photocoagulator with the laser beam stabilized, but the system is equally applicable using any other kind of beam. It is contemplated that the appended claims will cover any such modifications as fall within the true spirit and scope of this invention.

What is claimed is:

1. A stabilized visual system including fundus illumination and monitoring means simultaneously to illuminate and observe the fundus of an eye, eyetracker means capable of distinguishing between eye translation and rotational movements regardless of the refractive condition of the said eye and continuously measuring changes in position of the said eye, said eye tracker means generating output signals in response to the said changes which signals are a function of the said changes, coherent light beam generating means for generating a coherent input beam, input beam stabilization means positioned to receive the said input beam and to direct the said beam to a selected fixed location in the said eye, said input beam stabilization means including beam directing means and servo means connected to receive the said signals generated by said eyetracker means and move said beam directing means as a function of said changes in position of the said eye, thereby constantly directing the said beam to the said selected fixed locatin in the said eye regardless of eye movements.

2. A stabilized visual system including fundus illumination and monitoring means simultaneously to illuminate and observe the fundus of an eye, eyetracker means capable of distinguishing between eye translation and rotational movements regardless of the refractive condition of the said eye and continuously measuring changes in position of the said eye, said eye tracker means generating first and second output signals, said first output signal having a magnitude which is a function of the horizontal translational and rotational change of position of the said eye and said second output signal having a magnitude which is a function of the vertical translational and rotational change of position of the said eye, an input beam generating means for generating an eye treating beam, and a beam directing means for directing the said beam to a selected fixed location in the said eye comprising optical means positioned in the path of the said beam, said optical means including first and second spaced apart mirrors positioned serially in the path of said beam and each located in a position nominally optically conjugate to the nodal point of the eye, each of said mirrors being individually mounted for rotation about an axis therethrough, and first and second servo motors respectively mechanically connected to rotate the first and second mirrors about their respective axes, said first and second servo motors being respectively connected to receive said first and second output signals from the said eyetracker means, whereby the said first and second mirrors are rotated in response to the said first and second output signals respectively thereby constantly directing the said beam to the said selected fixed location in the said eye regardless of eye movements.

* * * * *